United States Patent [19]

Sarrine

[11] Patent Number: 5,251,786

[45] Date of Patent: Oct. 12, 1993

[54] BIOLOGICAL FLUID COLLECTION AND DELIVERY APPARATUS AND METHOD

[75] Inventor: Robert J. Sarrine, Beaumont, Tex.

[73] Assignee: Helena Laboratories Corporation, Beaumont, Tex.

[21] Appl. No.: 746,410

[22] Filed: Aug. 16, 1991

[51] Int. Cl.$^5$ .............................................. B67D 5/00
[52] U.S. Cl. ............................... 222/82; 222/206; 222/401; 128/764; 128/770; 604/205; 604/142; 604/411
[58] Field of Search .............................. 128/764, 770; 222/80-86, 207, 209, 211, 401, 400.8, 631-633; 604/140, 142, 411, 201, 205

[56] References Cited

U.S. PATENT DOCUMENTS

| | | | |
|---|---|---|---|
| 2,193,322 | 3/1940 | Lozier et al. | 604/201 X |
| 2,642,064 | 6/1953 | Lawshe | 222/83 X |
| 3,092,106 | 6/1963 | Butler | 222/88 X |
| 3,369,708 | 2/1968 | Hein | 222/89 X |
| 3,552,605 | 1/1971 | Hein | 222/479 X |
| 4,078,699 | 3/1978 | Soto | 222/89 |
| 4,121,735 | 10/1978 | Wittersheim | 222/83.5 |
| 4,808,381 | 2/1989 | McGregor et al. | 222/83.5 X |
| 4,976,925 | 12/1990 | Porcher et al. | 128/764 X |
| 5,163,583 | 11/1992 | Whitworth | 222/209 X |

Primary Examiner—Andres Kashnikow
Assistant Examiner—Kenneth DeRosa
Attorney, Agent, or Firm—Spencer, Frank & Schneider

[57] ABSTRACT

A biological fluid collection and dispensing apparatus for attachment to a test tube includes a pump and a cannula assembly including a fluid transfer cannula and a vent cannula housed partially within the pump. Biological fluid may be both collected and delivered with the apparatus, and the apparatus may remain attached to the test tube during processing of the collected biological fluid sample.

9 Claims, 3 Drawing Sheets

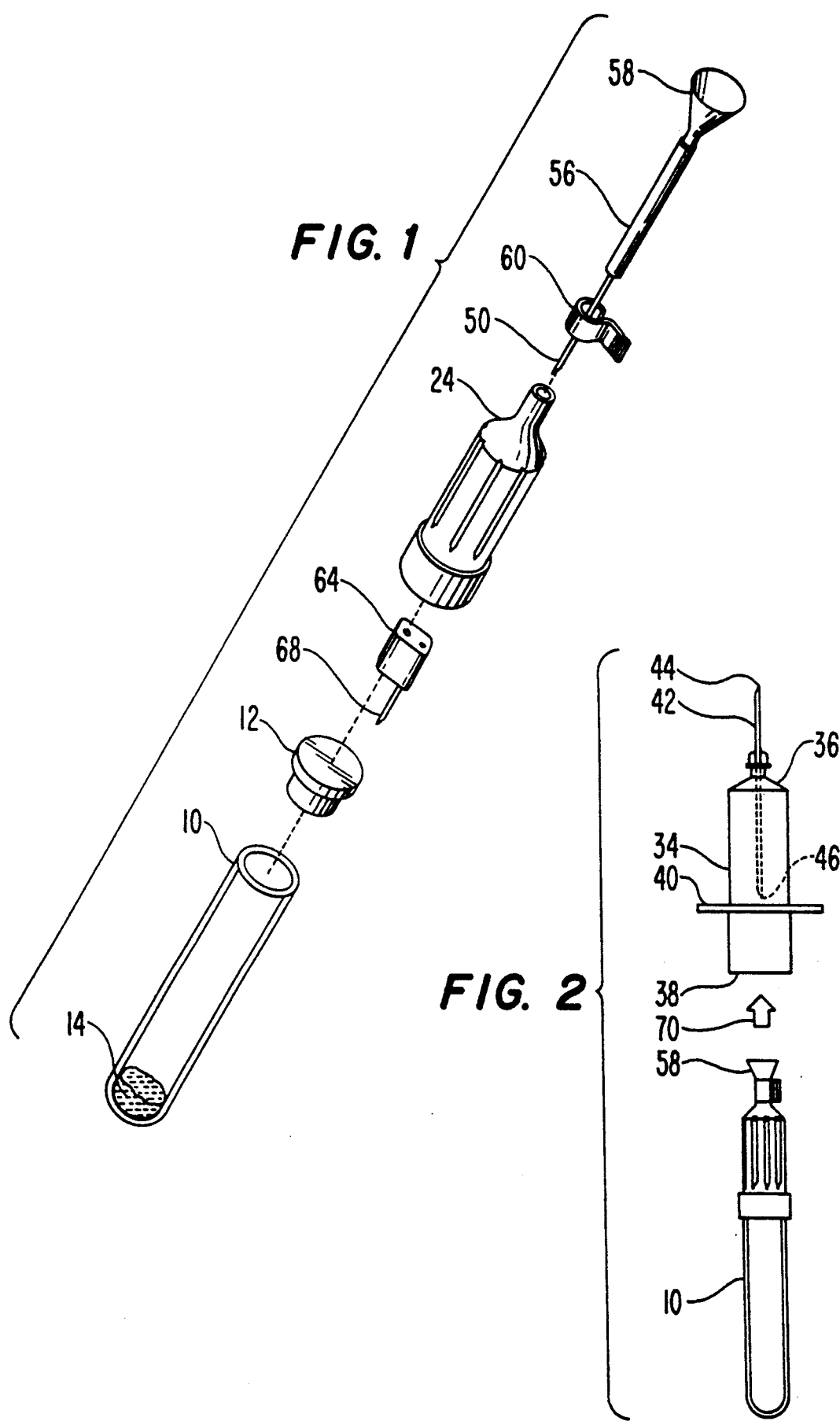

FIG. 5
FIG. 6
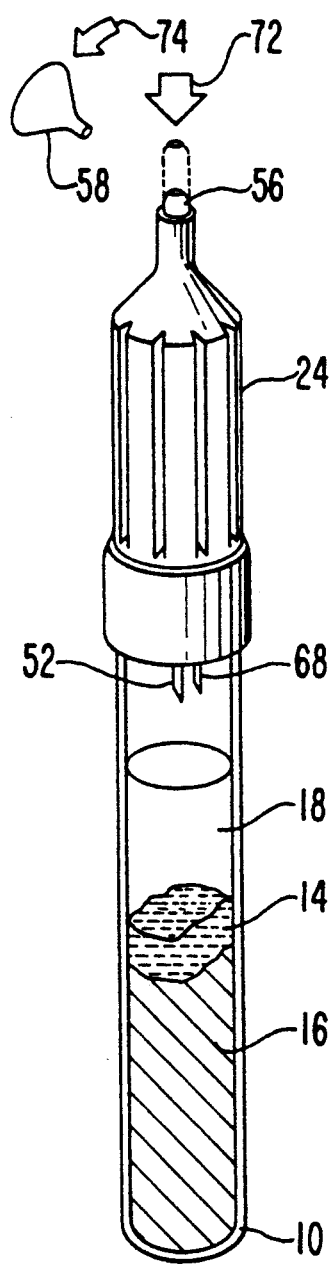
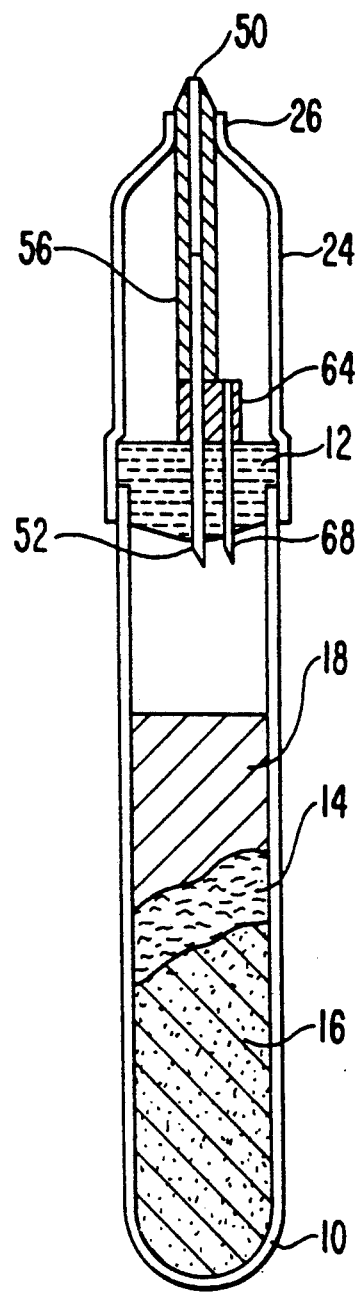

BIOLOGICAL FLUID COLLECTION AND DELIVERY APPARATUS AND METHOD

CROSS-REFERENCE TO RELATED APPLICATIONS

The present application includes subject matter in common with prior applications Ser. No. 07/504,597, filed Apr. 4, 1990, which is a continuation-in-part of application Ser. No. 7/382,760, filed Jul. 21, 1989, which is a continuation-in-part of application Ser. No. 07/208,447 filed Jun. 20, 1988, and prior applications Ser. Nos. 07/256,243 filed Sep. 30, 1988 and 07/089,275 filed Aug. 25, 1987, now U.S. Pat. No. 4,925,065, which were continuations of application Ser. No. 07/000,266 filed Jan. 2, 1987, now U.S. Pat. No. 4,811,866, all of which are hereby incorporated by reference.

BACKGROUND OF THE INVENTION

The invention relates generally to methods and apparatus for drawing or collecting blood or other biological fluid from a patient and thereafter dispensing the biological fluid in aliquots for analytical testing. More specifically, the present invention relates to a one-piece disposable apparatus including all of the features needed to draw such fluids and thereafter dispense the fluid.

The separation and analysis of chemical substances provides valuable quantitative and qualitative data for use by researchers and health care providers. Many assaying techniques have been developed which utilize sensitive chemical tests and sensitive instruments to detect both normal and abnormal components of biological fluids such as blood, urine and spinal fluid. In particular, the analysis of samples of these fluids reveals information which is critical to the proper diagnosis and treatment of many disorders. To perform such an analysis, a biological sample is typically withdrawn from the patient into a test tube or vacuum draw collection tube. The biological sample may be subjected to centrifugation. Then the biological sample is dispensed, in suitable aliquots, for testing. In the example of withdrawing blood from a patient, centrifugation separated the serum from the red blood cells and, thereafter, the amount of serum protein, protein-bound iodine, sodium, triglycerides, salicylate, uric acid and the like may all be determined through the analysis of the blood components.

After a biological sample is withdrawn from a patient into a test tube or collection tube, a technician must dispense aliquots or small quantity samples from the test tube. The test tube, of course, is initially sealed to prevent (a) contamination of the sample by ambient constituents and (b) to prevent substances in the sample from entering the atmosphere and/or adversely affecting the technician. Upon removing the conventional stopper from a test tube, the sample is again subject to possible contamination and a phenomenon known as aerosoling occurs. Aerosoling is the expulsion into the air, in the vicinity of the test tube, of minute quantities of the contents of the test tube and is caused by the force of removal of the stopper from the test tube. The removal of the stopper subjects the technician to the risk of exposure to whatever virus, bacteria or the like is carried in the biological sample.

The concern about exposure to the HIV virus has resulted in the adoption of numerous safety precautions in connection with the handling of biological fluids including products for dispensing biological fluids from a test tube without the need for removal of the stopper.

SUMMARY OF THE INVENTION

The present invention utilizes a new and different approach to the problems described above by eliminating the need for separate fluid withdrawal and fluid dispensing apparatus thus further minimizing the risk of contamination of the sample and further minimizing the risk of exposing the technician to the sample.

The present invention further relates to a new and improved apparatus which provides for both biological fluid withdrawal into a sealed container and biological fluid dispensing from the sealed container.

It is therefore an object of the invention to provide an efficient and inexpensive apparatus for biological fluid collection and dispensing.

It is a further object of the invention to provide a single assembly that performs both biological fluid collection and dispensing functions.

It is yet another object of the invention to provide a single apparatus for withdrawal of biological fluids such as blood, spinal fluids or the like into a sealed container, retaining such fluids for processing in the sealed container, and thereafter for dispensing the biological fluids in aliquots through the seal of the container.

The above and other objects are accomplished according to an embodiment of the invention by the provision of a biological fluid collection apparatus for attachment to a test tube including a flexible member such as a bulb pump, cannula means and cannula housing means, biological fluid being drawn through the cannula means into a sealed test tube, a portion of the cannula housing means being removed, and the biological fluid thereafter being dispensed through the cannula means.

BRIEF DESCRIPTION OF THE DRAWINGS

The foregoing objects and advantages of the invention, together with other objects and advantages which may be attained by its use, will become more apparent upon reading the following detailed description of the invention taken in conjunction with the drawings In the drawings, wherein like reference numerals identify corresponding components:

FIG. 1 is an exploded illustration of the present invention in conjunction with a blood collection tube or the like;

FIG. 2 is an exploded diagrammatic illustration of the use of the present invention such that blood or other biological fluid may be withdrawn from a patient;

FIG. 5 is a diagrammatic illustration of the removal of portions of the invention after the biological fluid has been subjected to processing such as centrifuging; and FIG. 6 is a cross-sectional illustration of the dispensing of the biological fluid according to the invention.

DETAILED DESCRIPTION OF THE INVENTION

Figure 3:
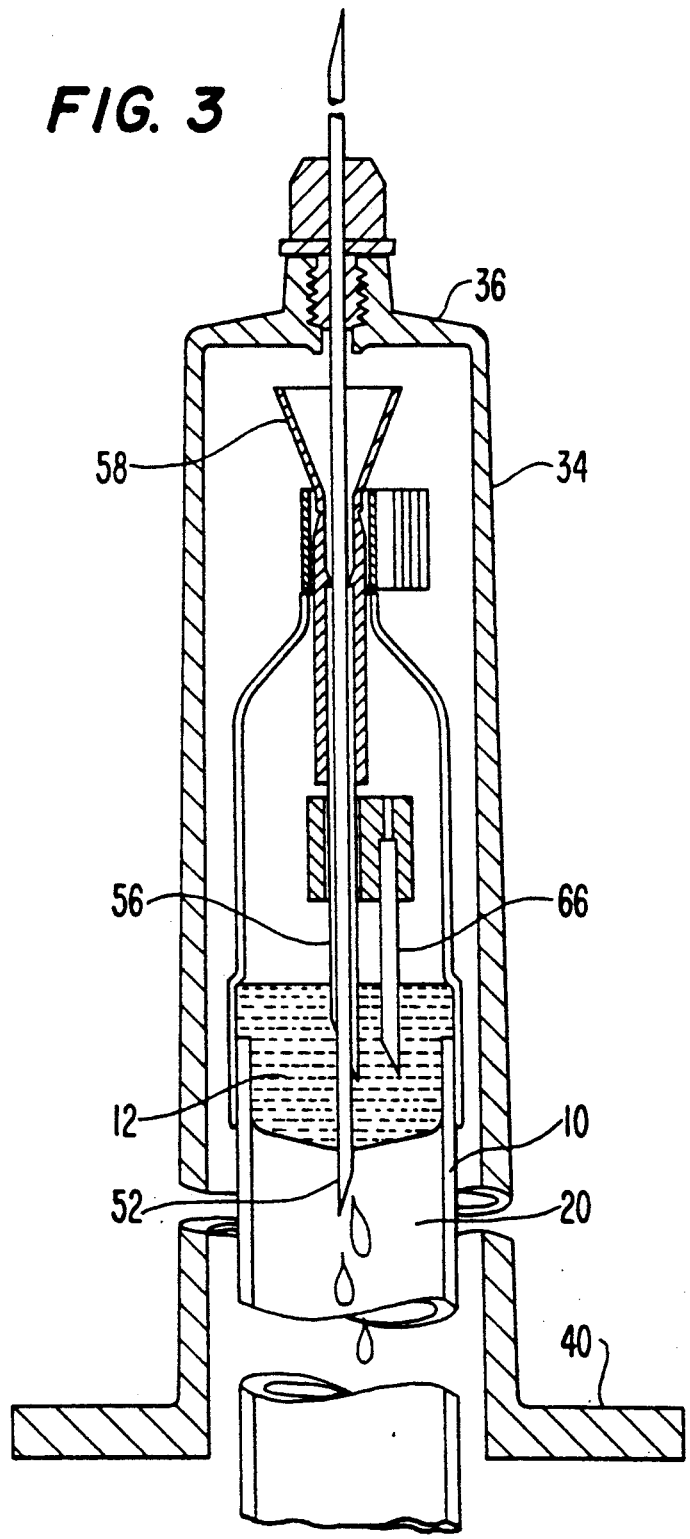
FIG. 3 is a cross-sectional view of the invention illustrating the withdrawal of a biological fluid from a patient.
Figure 4:
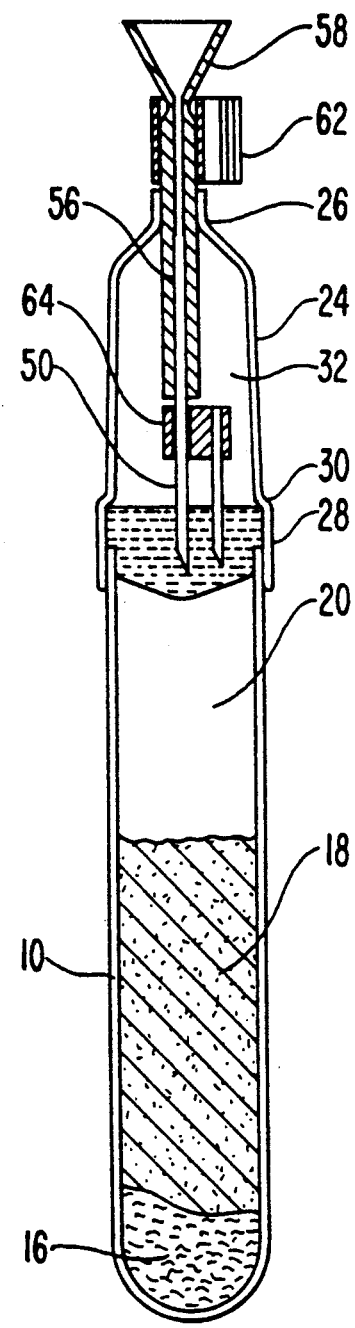
FIG. 4 is a cross-sectional view of the invention after biological fluid has been withdrawn from a patient.

Referring first to FIG. 1, the present invention is illustrated in exploded form to be attached to a test tube or collection tube 10 of the type which is sealed by a puncturable, reusable, resilient stopper or closure 12 as is conventional. Portions of the apparatus may be seen in greater detail in FIGS. 2–6. The sealed test tube may be under vacuum, such as a Vacutainer test tube marketed by Becton-Dickinson, and if the test tube is to be used for blood serum separation, then, in addition to an anticoagulant in the test tube as is conventional, a conventional gel-like separator plug 14 is included in the test tube. Referring briefly to FIGS. 4–6, if blood has been introduced into the test tube and thereafter the blood centrifuged, the red blood cells 16 will be positioned in the bottom of the test tube, on one side of the separator plug 14, and the serum 18 will be on the opposite side of the plug 14. An unfilled space or air gap 20 may exist between the serum and the underside of the stopper 12.

A pump means 24 is mounted to the test tube 10. Specifically, with reference to FIGS. 4, 5 and 6, a pump means is illustrated in the form of a flexible, elongated, resilient bulb having a first, preferably constricted end 26 and a second open end 28. A shoulder 30 is formed in the bulb intermediate the two ends, the shoulder being adjacent the second end 28, and the shoulder and second end are configured to frictionally receive and retain the closed top of the test tube 10. A cavity 32 is defined by the interior of the pump means 24.

When it is desired to withdraw biological fluid from a patient, a generally conventional multiple-draw collection tube holder 34 is utilized, the holder having a closed first end 36 and an open second end 38 with a radially outwardly projecting flange 40 therebetween. In the present invention the portion of the holder 34 between the flange 40 and the second end 38 would be of increased axial length compared to a conventional holder. An elongated cannula 42 having opposed, sharpened tips 44, 46, respectively, extends through the closed end 36 of the holder 34 such that tip 44 extends outwardly of the holder and tip 46 extends inwardly of the holder. The flange 40 is to be grasped between the fingers of the technician during insertion of the apparatus of the present invention into the holder for the provision of controlled relative movement between the parts of the invention as will be explained in greater detail. The provision of such a flange is also conventional for a multipledraw tube holder.

The apparatus of the present invention includes a first cannula 50, which may also be considered a fluid transfer or flow path, the cannula having a sharpened tip 52 at one end. The first cannula 50 extends through an elongated hollow cylindrical cannula housing 56, the cannula housing having second portion extending through the constricted open first end 26 of the pump means. The cannula housing 56 terminates in a first portion exteriorly of the pump means 24, such as a funnel or conical shaped portion 58 which is severable from the cylindrical portion of the cannula housing. A collar 60 surrounds the cannula housing 56 exteriorly of the pump means 24, the collar including a tab or radial extension 62 to facilitate removal of the collar. One side of the collar contacts the end 26 of the pump means 24 and the other side of the collar contacts the funnel 58 such that relative movement of the funnel toward the pump means is precluded when the collar is positioned between the pump means and the underside of the funnel.

The first cannula 50 extends through an elongated first aperture in a cannula support member 64, and first cannula 50 is fixed longitudinally relative to the cannula support. The cannula support member includes a second aperture, laterally spaced from the first aperture, and a vent cannula 66, having a sharpened tip or end 68, extends through the second aperture in the cannula support member. First cannula 50 and vent cannula 66 may be considered as cannula means. Cannula housing 56, including funnel portion 58, and cannula support member 64 may be considered as cannula housing means.

The operation of the apparatus will now be explained. With the collar 60 spaced longitudinally between the first end 26 of the pump means and the underside of the funnel 58, the sharpened tip 52 of the cannula and the sharpened tip 68 of the vent cannula are both positioned within the rubber stopper or closure 12 of the test tube 10. The first use of the apparatus of the present invention is to withdraw biological fluid such as blood from a patient. The apparatus is inserted interiorly of the holder 34 illustrated in FIGS. 2 and 3 by moving the test tube 10 longitudinally from the holder open end 38 inwardly toward the holder closed end 36. For this purpose the flange 40 on the cylinder may be grasped by the technician using the present invention. The relative longitudinal movement causes the top of the funnel 58 to contact the interior of the first end 36 of the holder 34 and continued movement of the test tube causes the cannula housing 56 and cannula 50 longitudinally toward the test tube until the collar 60 "bottoms out" or abuts both the underside of the funnel 58 and the first end 26 of the pump means 24. This abutting position is illustrated in FIG. 3 and, during the movement of the housing and cannula to such position, the sharpened tip 52 of the cannula will extend completely through the stopper 12. Referring briefly to FIG. 2, this movement is illustrated diagrammatically by arrow 70. Thus relative axial movement has been described but it must be realized that one of the parts may be maintained stationary and the other part moved in relation to the stationary part or that both parts may be moved toward each other. The movement of the first cannula 50 and cannula housing 56 as described, however, does not cause the vent cannula tip 68 to emerge through the stopper 12.

The cannula tip 44 of the holder 34 is inserted into the patient and biological fluid is withdrawn with the fluid flowing through the second cannula 42, through the funnel 58, through the first cannula 50 and into the interior of the test tube 10.

After the completion of withdrawal of biological fluid from the patient (and the cannula 42 withdrawn from the patient), the apparatus is withdrawn from the holder 34 and then the test tube, with the pump means 24 still attached, may be subjected to centrifuging operations.

When it is desired to remove aliquots of the biological fluid from the test tube, several steps are appropriate. First, the collar 60 is removed from the cannula housing 56 such as by pulling the tab 62 radially outwardly. Then the funnel and cannula housing 56 are moved manually in a longitudinal direction inwardly until the underside of the funnel 58 abuts against the first end 26 of the pump means 24. This movement causes the cannula housing 56 to contact the cannula support member 64, and continued movement of the funnel causes the cannula support member 64 to move axially toward the test tube stopper 12 until the bottom of the cannula support member 64 contacts or approaches the top of the stopper 12. The degree of movement of the cannula support member is such that the tip 68 of the vent cannula will extend completely through the stopper 12. This relative position is illustrated in FIGS. 5 and 6. Once the axial or longitudinal movement of the cannula housing 56 and funnel 58, and cannula support member 64 have caused vent cannula tip 68 to pierce through the stopper 12, funnel portion 58 may be removed from (e.g., broken-away) from the cylindrical portion of the cannula housing, and the funnel portion discarded. Arrow 72 (FIG. 5) illustrates, diagrammatically, the longitudinal movement of the cannula housing 56 and arrow 74 illustrates, diagrammatically, the removal of the funnel 58 from the cannula housing 56.

Then the test tube with pump means attached is inverted and the pump means actuated. In the illustrated embodiment the flexible bulb would be compressed by a laterally inward force. Compression of the bulb causes air within the pump means 24 to flow through the vent cannula 66 into the interior of the test tube 10. This tends to pressurize the fluid within the test tube such that biological fluid is pumped outwardly through the first cannula 50 to be dispensed in a drop-by-drop manner. After the fluid has been dispensed, the apparatus is again "inverted" thus restoring the apparatus to its original, upright position, and the pump means 24 is released. Ambient air is drawn through the first cannula 50 into the air space 20 interiorly of the test tube 10 and flows upwardly through vent cannula 66 to again fill the pump means 24 with air. Thereafter, by again inverting the apparatus and actuating the pump means 24, fluid may be dispensed through first cannula 50.

In the preferred embodiment, all cannulas are formed of stainless steel and the remaining components (other than the glass test tube and rubber stopper) may be formed of plastic. More specifically, the pump means 24 may be formed of a resilient, flexible plastic such as polyethylene and the remaining plastic members such as the cannula housing 56, including the funnel 58, collar 60, and the cannula support member may preferably be formed of styrene. The foregoing materials are exemplary for the purpose of illustrating the principles of the present invention and thus the foregoing should not be construed as limitations on the present invention.

It should be further understood that the apparatus of the present invention is adapted to be attached to a conventional test tube by the technician. Alternatively, the apparatus of the present invention may be attached to a test tube at the time the test tube is initially placed under partial vacuum.

It will be understood that the above description of the present invention is susceptible to various modifications, changes, and adaptations, and the same are intended to be comprehended within the meaning and range of equivalents of the appended claims.

What is claimed is:

1. Apparatus for drawing biological fluid from a patient into a test tube, the test tube being sealed with a puncturable closure, and for thereafter dispensing the biological fluid through the puncturable closure and from the test tube comprising:

a flexible member adapted to be attached to said test tube;

cannula housing means positioned relative to said flexible member, said cannula housing means having first and second portions;

a first cannula supported by said cannula housing means second portion having a tip insertable through the puncturable closure;

said cannula housing means first portion for receiving a second cannula, whereby said second cannula is positioned within the bore of said first cannula, such that biological fluid from a patient flows through said cannula housing means and said first and second cannulas into the sealed test tube; and said cannula housing means first portion being removable from said cannula housing means second portion whereby upon flexing said flexible member, biological fluid flows from the sealed test tube through said first cannula.

2. The apparatus of claim 1 wherein said flexible member is a pump means.

3. The apparatus of claim 1 further including a test tube having a closure and wherein said first cannula tip is inserted into said test tube closure.

4. A biological fluid collection and dispensing apparatus for attachment to a test tube comprising:

a flexible bulb pump; and cannula means disposed at least partially within the bulb pump, the cannula means including a fluid transfer cannula extending axially relative to the bulb pump and a vent cannula disposed adjacent to the fluid transfer cannula, and cannula housing means movably mounted relative to said bulb pump for supporting the cannula means.

5. The apparatus of claim 4 wherein said cannula housing means includes a first severable portion and a second portion attached to said first portion.

6. The apparatus of claim 5 wherein said cannula housing means includes a removable collar for preventing premature dispensing of biological fluid from said test tube.

7. A method of using the apparatus of claim 4, comprising:

attaching a test tube having a resilient stopper to the apparatus so that a portion of the fluid transfer cannula pierces and extends through the stopper completely;

withdrawing fluid from a patient through the fluid transfer cannula into a test tube;

collecting a quantity of biological fluid into the test tube through the fluid transfer cannula;

removing a portion of the cannula housing means;

moving the cannula housing means towards the test tube so that the vent cannula pierces completely through the stopper; and flexing the bulb pump to deliver a portion of the biological fluid in the test tube through the fluid transfer cannula.

8. The apparatus of claim 4 wherein said fluid transfer cannula and said vent cannula partially pierce a stopper of a test tube when the apparatus is initially attached to a test tube.

9. The apparatus of claim 4 wherein the cannula housing means includes a cannula support member having said vent cannula therethrough, and movement of said cannula housing means moves the cannula support member.

* * * * *